United States Patent [19]

Moss

[11] Patent Number: 4,642,092

[45] Date of Patent: Feb. 10, 1987

[54] GASTROINTESTINAL ASPIRATING DEVICE WITH SUCTION BREAKERS

[76] Inventor: Gerald Moss, R.D. #1, West Sand Lake, N.Y. 12196

[21] Appl. No.: 679,688

[22] Filed: Dec. 10, 1984

[51] Int. Cl.⁴ .......................................... A61M 25/00
[52] U.S. Cl. ....................................... 604/43; 604/96; 604/280
[58] Field of Search ..................... 604/43, 45, 96, 93, 604/264, 266–268, 280

[56] References Cited

U.S. PATENT DOCUMENTS

| | | | |
|---|---|---|---|
| 2,642,873 | 6/1953 | Rice | 604/267 |
| 2,930,378 | 3/1960 | Buyers | 604/268 X |
| 3,495,595 | 2/1970 | Soper | 604/43 X |
| 3,810,471 | 5/1974 | Truhar | 604/45 |
| 4,114,625 | 9/1978 | Onat | 604/96 |

Primary Examiner—Stephen C. Pellegrino
Attorney, Agent, or Firm—Schmeiser, Morelle & Watts

[57] ABSTRACT

In an aspirating and feeding device for insertion into a patient's body there is an aspirating lumen and a feeding lumen. A set of primary and secondary orifices are placed through the tube for communication between the aspirating lumen and the exterior of the tube. The size of the primary and secondary orifices relate to each other such that the secondary orifices are smaller than the primary orifices. The feeding lumen has an external end portion to be disposed outside the body and an internal end portion to be disposed in the proximal segment of the small bowel. The internal end portion having an orifice therein for the discharge of food.

11 Claims, 3 Drawing Figures

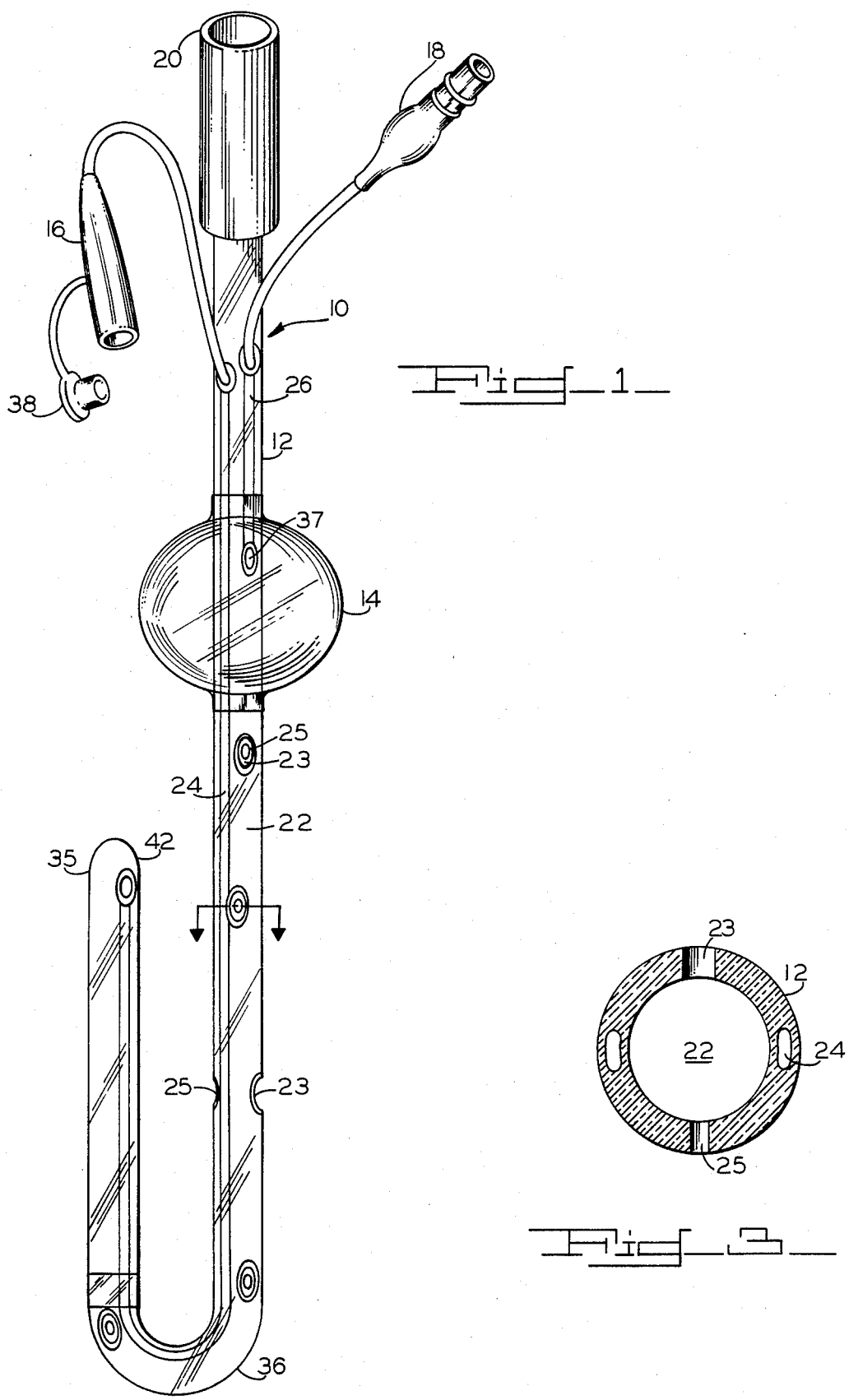

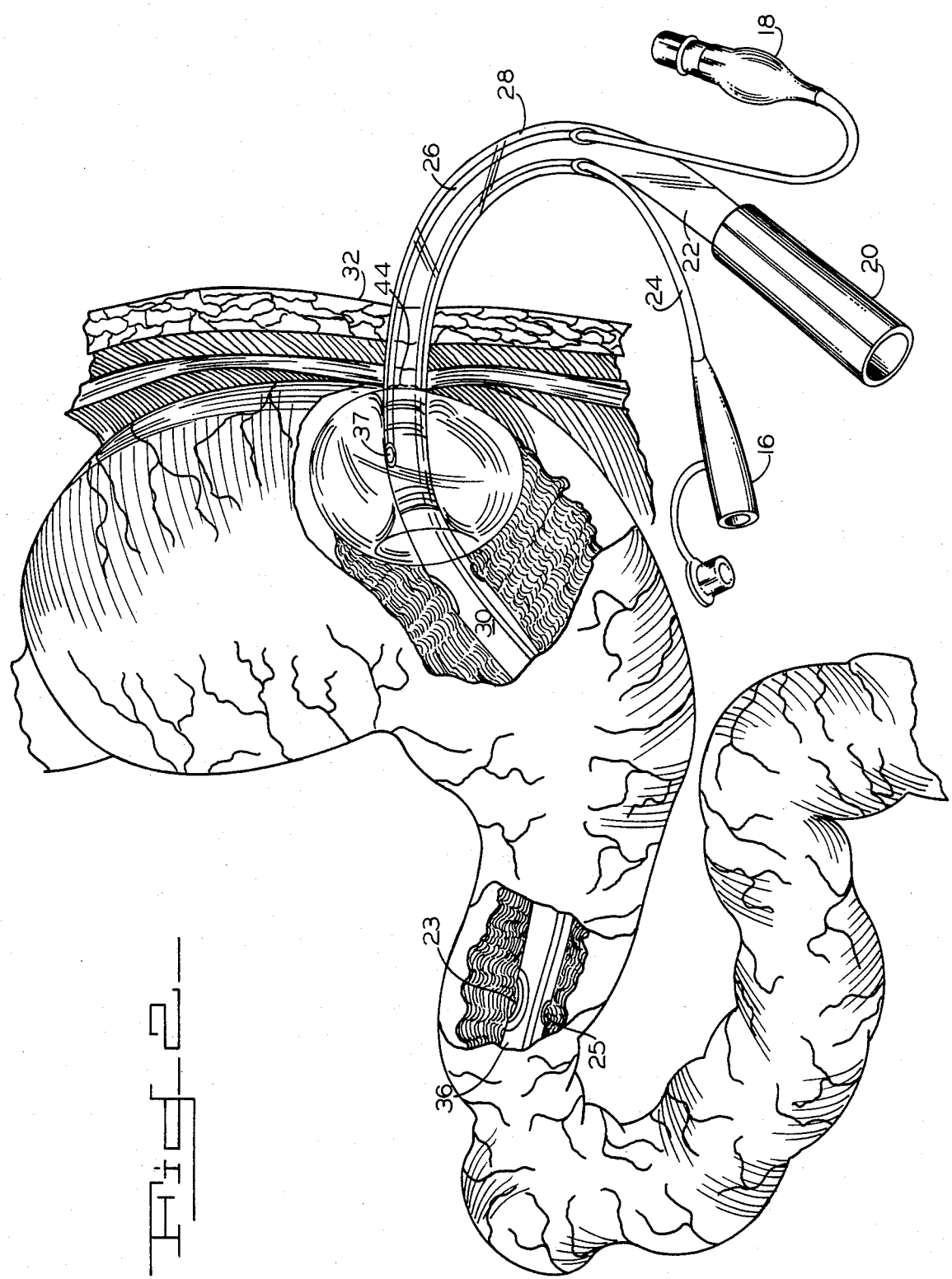
Fig_2

GASTROINTESTINAL ASPIRATING DEVICE WITH SUCTION BREAKERS

BACKGROUND AND SUMMARY OF THE INVENTION

This invention relates to a gastrointestinal aspirating device with suction breakers and a method of use in treating patients.

Post-operatively, gastrointestinal functions usually deteriorate. The causes of this deterioration are varied and include such factors as the use of anesthesia or pain killing drugs, and the handling of the bowel during the operation. Additionally, air swallowed by the patient contributes to gastrointestinal malfunctions since the gas is inefficiently propelled through the digestive tract. This causes a problem commonly known as abdominal distention which not only impairs bowel function and interferes with the rate of absorption of nutrients through the bowel, but often prevents the patient from breathing deeply or coughing, which can lead to severe pulmonary difficulties. In severe cases, the pressure caused by the abdominal distention has been known to break open the patient's wound. One of the indirect effects of abdominal distention is the fact that due to the pain associated with it, and the lesser rate of bowel absorption, the patient often becomes undernourished which slows the healing process. It has, therefore, been a long-standing objective of the medical profession to prevent abdominal distention while providing sufficient nutrition in order to speed the patient's recovery.

In order to meet this need, a large variety of aspirating tubes have been developed. A significant number of these tubes also include feeding means such as disclosed in my patent application, Ser. No. 312,215 filed 10-19-81/CIP Ser. No. 585,632 filed 3-8-84, the disclosure of which is incorporated by reference into this patent application. While all of these devices are effective to varying degrees, there is one main difficulty which virtually all these inventions have encountered and none have yet effectively been able to solve. This problem stems from the fact that most of these tubes when placed within the patient, are in contact with or in the area of various pliable membranes which have a tendency to be drawn into the aspirating orifices when suction is applied through the tubes. Thus, the aspirating ability of the tube decreases in direct proportion with the number of orifices which are blocked.

Aspirating orifices may also become blocked or plugged by the material which is to be aspirated. However, this type of blocking or plugging can generally be avoided by utilizing orifices which are sufficiently large in area to meet the expected flow. In order to obtain maximum flow through these orifices, their area is equal to the cross-sectional area of the lumen within the tube. Any increase in the area of the orifices beyond this cross-sectional area would yield no beneficial result since the area of the lumen would then simply act as the flow limiting factor. Thus, one generally chooses a tube having a diameter which is appropriate for the patient being administered to and this limit often sets the parameters for the size of the lumen and the associated aspirating orifices.

While these larger orifices are needed in order to assure desirable flow rates without plugging by the materials to be aspirated, due to their area, they form a strong bond when they attach to an organ's inner lining. Once one of the orifices attach to the organ wall, greater suction develops through the other orifices. This increase in suction causes other orifices to be drawn to the inner walls and also become occluded which, again, increases the suction applied to the remaining orifices. Thus, with those inventions heretofore known, a chain reaction occurs which results in the blocking of virtually all the aspirating orifices.

In order to disengage the aspirating orifices from the inner walls, it was often necessary to stop the suction until the tube had broken free. While this would normally enable the normal movements of the body and organs to eventually disengage the tube, there are two major drawbacks which render this procedure undesirable. First, and most important, is the fact that during the time that the suction is not being applied, noxious materials within the patient's body may be propelled beyond the range of the tube, and therefore, be unrecoverable once the suction is reinstituted. Secondly, the input of time which is necessary in order to monitor and disengage the tube as needed can become substantial. Thus, time which could be utilized more effectively is spent trying to maintain the tube at an acceptable level of operation.

In order to overcome this difficulty, some tubes have been designed with aspirating orifices placed at different locations circumferentially around the tube. Although this arrangement has helped to lessen this difficulty in some situations, it is still common, primarily due to the strong adjesive powers of the large orifices to have an unacceptable number of these orifices blocked.

In my feeding and aspirating tube which has been incorporated by reference above, there is an aspirating orifice in the proximal segment of the small bowel and a feeding orifice downstream from the aspirating orifice. Since the proximal segment of the small bowel is a small diameter conduit, this aspirating orifice effectively removes most of the matter entering from the stomach. In addition, this aspirating orifice also serves to withdraw any food which, administered through the feeding orifice, backs up due to overfeeding. Due to the important functions of this aspirating orifice, it is obviously essential that any clogging or blocking of this orifice be avoided.

For these reasons, I began looking for different ways to either prevent these aspirating orifices from attaching to the wall lining or provide a way to automatically disengage them once they had attached. As indicated by the procedure wherein the suction is completely eliminated, a reduction of the suction created a situation wherein the natural movement of the wall lining and the tube was sufficient to disengage the aspirating orifice. However, while I wished to reduce the holding force through these orifices sufficiently to allow them to disengage, I also wanted to maintain aspiration to prevent noxious materials from passing beyond the range of the tube. After much deliberation, I began experimenting with a secondary set of orifices, the main purpose of which would be to reduce the level of suction within the lumen when the primary orifices were occluded by the wall lining. When the aspirating orifices are occluded, the gas and liquid inflow through the secondary orifices causes a marked decrease in the level of suction within the aspirating lumen. This reduced suction within the lumen is sufficient to allow the larger aspriating orifices to break free from the wall lining. If the smaller orifices become attached, they are easily disengaged by the normal movement of the lining and tube since the reduced area of these smaller orifices results in less holding power to the wall lining. These suction breaker orifices had to be large enough to provide a sufficient drop in suction yet small enough that the holding power against the wall linings was ineffectual. My preferred size range for these orifices was from ⅓ to 1/20 of the surface area of the larger aspirating orifices, or the cross-sectional area of the aspirating lumen which should be equal.

It is, therefore, an object of this invention to provide an aspirating device which is effective in avoiding abdominal distention without frequent monitoring.

It is also an object of this invention to provide as aspirating device which is less subject to being occluded than prior devices.

It is yet another object of this invention to provide a feeding and aspirating device which prevents overfeeding through the use of these improved aspirating means.

Briefly described, the preferred embodiment of this invention consists of a tube having a feeding lumen and as aspirating lumen which are inserted into the patient's body and secured thereto. Both the aspirating lumen and the feeding lumen have orifices so as to communicate with various sites within the patient's body. There are two sets of aspirating orifices. One set of primary orifices act as main aspirating sites, while the secondary set of orifices act as suction breakers for the primary aspirating orifices. At predetermined points along the tube, there are placed a pair of orifices, one primary and one secondary orifice. When in its secured position, the feeding orifice is positioned in the proximal segment of the small bowel. Upstream from the feeding orifice, and before the pyloric sphincter, at least one primary and one secondary orifice communicates with the proximal segment of the small bowel. In the stomach, the same aspirating lumen has orifice pairs for aspirating the stomach.

BRIEF DESCRIPTION OF THE DRAWINGS

FIG. 1 is an elevational view of the gastrointestinal aspirating device.

FIG. 2 shows the invention disposed within a patient's body.

FIG. 3 is a cross-sectional view taken through lines 3—3 of FIG. 1.

DETAILED DESCRIPTION OF THE DRAWINGS

FIG. 1 shows the gastrointestinal device generally designated as 10. The device 10 has a main elongated tube 12. Three lumens run through the tube 12. Towards one end of the tube, which will become the external end portion when placed within the patient, two of the lumens separate from the tube 12, thus leaving three individual tubes, each having a single lumen. At the end of each of the tubes is an open-ended attachment member. A balloon 14 is attached around the tube 12 at a site where all three lumens are within the tube 12.

Since the device is used in conjunction with the internal organs of the body, it should be made of a biocompatible material. I have found that both polysiloxane and polyurethane serve this purpose very well.

FIG. 3 shows the tube 12 in cross-section, revealing two of the three lumens. The aspirating lumen 22, which is the largest of the three lumens, is centrally located within the tube 12. The feeding lumen 24 is located within the wall of the tube 12. FIG. 3 also discloses a primary orifice 23 and a secondary orifice 25 through the tube wall into the aspirating lumen 22. This orifice pair work in conjunction with each other to break the suction within aspirating lumen 22 to prevent the patient's inner membranes from being drawn to the tube, thereby blocking the aspirating orifices.

FIG. 2 shows the gastrointestinal device positioned within the body. When so placed, several portions of the device can be described based upon their relationship to the anatomy. These portions are: the external end portion 28 which is outside of the body; the mid-portion 30 which extends from the body wall 32 to the pyloric sphincter 34; and the internal end portion 36 which extends from the pyloric sphincter to the internal end 35 of the device in the proximal segment of the small bowel.

Along these various portions are orifices each of which provides a passageway from a lumen to the outside of the tube. Externally, each lumen ends in an attachment such that the feeding attachment 16 corresponds to the feeding lumen 24; the inflation attachment 18 corresponds to the inflation lumen 26; and the aspirating attachment 20 corresponds with the aspirating lumen 22.

The aspirating attachment 20 at the external end of the aspirating lumen is adapted to connect to a source of suction. Orifices in the aspirating lumen are in the mid-portion and the internal end portion of the tube. These orifices consist of a set of primary orifices 23 and secondary orifices 25. At each point along the tube where there is a primary orifice 23, there is also a corresponding secondary orifice 25. Should the primary orifices 23 become attached to the internal membrane of the patient's body, the secondary orifices will serve to break the suction thereby reducing the holding power through the primary orifices so that they may breakaway. In the preferred embodiment, the center points of a primary orifice and its corresponding secondary orifice are substantailly equi-distant from the internal end 35 of the device. Nevertheless, the orifices in an orifice pair can be offset from each other. However, if the secondary orifices are down stream or distal to the primary orifices, the suction breaking affect will be negligible. Similarly, while the preferred embodiment shows the primary and secondary orifices placed 180° apart from each other, variations can be made and various degrees of effectiveness can be obtained depending upon the type of membrane in the internal organ in which the tube is placed.

The relationship between the sizes of the primary and secondary orifices is critical. The secondary orifices act as suction breakers and do not become strongly secured to the inner membranes because their size is sufficiently small enough to prevent any significant holding power. Yet, they must be large enough, or plentiful enough to allow an ample amount of air to be aspirated into the lumen 22 to substantially reduce the suction within the lumen when the primary orifices become blocked. Obviously, therefore, the size of the secondary orifices can be changed with varying degrees of success.

Generally, I have found that where the primary orifices are equal in size to the cross-sectional area of the aspirating lumen, the secondary orifices should range from ⅓ to 1/20 of that area.

Both the stomach and the proximal segment of the small bowel are aspirated through the various orifices opening into aspirating lumen 22. The aspirating lumen is occluded three inches from the internal end of the tube 12. By having the last pair of aspirating orifices at least three inches from the feeding orifice, the feeding solution during a normal feeding period will not flow retrograde sufficiently to be aspirated. However, should there be a blockage, the feeding solution will flow retrograde three inches and be aspirated before there is a detrimental buildup of pressure within the proximal segment of the small bowel.

The inflation attachment 18 at the external end of the inflation lumen 26 is adapted to receive a syringe. The inflation orifice 37 in the tube communicates within the inside of the balloon 14. Thus, the balloon cam be inserted into the body in its deflated position and then, as shown in FIG. 2, can be inflated just inside the stomach.

The feeding attachment 16, which is located at the external end of the feeding lumen 24 is adapted to receive a male luer fitting. Connected to the feeding attachment is a sealing cap 38 which serves to close the external end of the lumen when it is not in use. The feeding lumen travels almost the entire length of the tube, 12, ending at a feeding orifice in the side of the tube. This opening is in the side of the tube in order to enable the internal end 35 of the tube to have a rounded tip 42 which facilitates insertion. In the preferred embodiment of this invention, the feeding orifice is three inches closer to the internal end than the last aspirating orifice.

Procedurally, the internal end of this device is pulled through a stab wound which is made in the abdominal wall. A perforation is then made in the stomach wall, and the internal end is carefully inserted. The rounded tip 42 is then advanced out from the stomach into and down the intestine until a balloon 14 fully enters the stomach. The balloon is then inflated with 10–30 ml. of sterile water. Slight traction is applied to the external portion of the device, sandwiching the stomach wall between the balloon and the abdominal wall. The device is then anchored with a suture 44 to the abdominal skin at the point of exit, as shown in FIG. 2.

In operation, the suction aspirates both the stomach and the proximal segment of the small bowel. Should the suction through the aspirating lumen 22 draw the lining of either the stomach or the proximal segment of the small bowel into one of the primary orifices 23, the secondary orifices will not only continue to provide some aspiration to the site, but more importantly serve to reduce the suction pulling the lining into the primary orifices. This aids in disengaging the inner membrane from the primary orifice, thereby increasing aspiration and also avoiding damage to the membrane. Since the body deposits a large amount of digestive juices into the small bowel, the aspiration of the bowel draws these juices through the aspirating lumen which keeps the lumen clear. To feed the patient, a feeding solution is administered through the feeding lumen 24 and exits through the feeding orifice at the internal end 35 of the tube 12. Should an excess amount of feeding solution be administered to the patient, it will flow retrograde to the aspirating orifices in the proximal segment of the small bowel, thus preventing overfeeding.

Changes and modifications in the specifically described invention can be carried out without departing from the scope of the invention which is intended to be limited only by the scope of the appended claims.

What is claimed:

1. A feeding and aspirating device for insertion into a patient's body, comprising:

a single walled tube, having an aspirating lumen and a feeding lumen therein, said aspirating lumen having an external end portion to be disposed outside the body, said feeding lumen also having an external end portion to be disposed of outside the body, and having an internal end portion to be disposed in the proximal segment of the small bowel, said internal end portion having an orifice therein for the discharge of food; and a set of primary aspirating orifices through said single walled tube for constant communication between the aspirating lumen and the exterior of the tube; and a set of secondary orifices through said single walled tube for constant communication between the aspirating lumen and the exterior of the tube, said secondary orifices having openings which are positionally fixed with relation to and smaller than the primary aspirating orifices.

2. The invention of claim 1 wherein the secondary orifices have an opening less than or equal to ⅓ the size of the opening of the primary orifices.

3. The invention of claim 2 wherein at least one secondary orifice is more proximal to the external end portion of the aspirating lumen than any of the primary orifices.

4. The invention of claim 3 wherein all of the secondary orifices are more proximal to the external end portion of the aspirating lumen than any of the primary orifices.

5. The invention of claim 1 wherein each secondary orifice corresponds to a primary orifice and is substantially equi-distant from the external end portion of the aspirating lumen as is its corresponding primary orifice.

6. The invnention of claim 5 wherein each secondary orifice is positioned 180° around the tube from the corresponding primary orifice.

7. An aspirating device for insertion into a patient's body, comprising:

a tube having an aspirating lumen therein, said aspirating lumen having an external end portion to be disposed outside the body;

a set of primary aspirating orifices in the tube for communication between the aspirating lumen and the exterior of the tube; and a set of secondary orifices in the tube for communication between the aspirating lumen and the exterior of the tube, the opening of said secondary orifices being smaller than the opening of the primary orifices, each secondary orifice corresponding to a primary orifice and being substantially equi-distant from the external end of the aspirating lumen as the primary orifice to which it corresponds.

8. The invention of claim 7 wherein the opening of the secondary orifices is less than or equal to ⅓ the size of the opening in the primary orifices.

9. The invention of claim 8 wherein at least one secondary orifice is more proximal to the external end portion of the aspirating lumen than any of the primary orifices.

10. The invention of claim 9 wherein all the secondary orifices are more proximal to the external end portion of the aspirating lumen than any of the primary orifices.

11. The invention of claim 7 wherein each secondary orifice is positioned 180° around the tube from the corresponding primary orifice.

* * * * *